(12) United States Patent
Fearnot et al.

(10) Patent No.: US 6,565,597 B1
(45) Date of Patent: May 20, 2003

(54) STENT ADAPTED FOR TANGLE-FREE DEPLOYMENT

(75) Inventors: Neal E. Fearnot, West Lafayette, IN (US); Brian D. Choules, West Lafayette, IN (US); Matthew S. Waninger, Frankfort, IN (US); Michael P. DeBruyne, Bloomington, IN (US)

(73) Assignees: MED Institute, Inc., West Lafayette, IN (US); Cook Incorporated, Bloomington, IN (US)

(*) Notice: Subject to any disclaimer, the term of this patent is extended or adjusted under 35 U.S.C. 154(b) by 141 days.

(21) Appl. No.: 09/617,352

(22) Filed: Jul. 17, 2000

Related U.S. Application Data

(60) Provisional application No. 60/144,303, filed on Jul. 16, 1999.

(51) Int. Cl.[7] .................................................. A61F 2/06
(52) U.S. Cl. ...................... 623/1.14; 623/1.13; 623/1.15
(58) Field of Search ............................... 623/1.13–1.15, 623/1.36, 903

(56) References Cited

U.S. PATENT DOCUMENTS 5,035,706 A * 7/1991 Giantureo et al. .......... 606/198
5,593,417 A * 1/1997 Rhodes ....................... 606/191
5,868,781 A * 2/1999 Killion ........................ 606/198
6,036,725 A * 3/2000 Avellanet ................... 623/1.14
6,042,605 A * 3/2000 Martin et al. .............. 623/1.13

FOREIGN PATENT DOCUMENTS

| EP | 0701800 | 3/1996 |
| WO | 9853761 | 12/1998 |
| WO | 9929262 | 6/1999 |

* cited by examiner

Primary Examiner—Corrine McDermott
Assistant Examiner—Javier G. Blanco
(74) Attorney, Agent, or Firm—Charles W. Agnew

(57) ABSTRACT

An expandable stent prosthesis is disclosed in which the apices of the bends located at at least one end of the stent are individually twisted at an angle to the circumference of the stent to form a fan blade-like arrangement when viewed from that end. The fan blade-like arrangement allows the stent to expand from the compressed condition during deployment such that likelihood of a strut or bend of the stent become entangled with a barb or adjacent strut or bend, is reduced. In one embodiment of the invention, the fan blade-like arrangement results from plastically deforming the individual apices, while in another embodiment, the apices are twisted into the fan blade-like arrangement during the loading process, such as by use of a suture thread to pull the apices into alignment.

25 Claims, 3 Drawing Sheets

STENT ADAPTED FOR TANGLE-FREE DEPLOYMENT

CROSS-REFERENCE TO RELATED APPLICATIONS

This invention relates to medical devices, more particularly to expandable stents. This application claims priority to U.S. Provisional Patent Application Ser. No. 60/144,303 filed Jul. 16, 1999.

BACKGROUND OF THE INVENTION

Vascular graft prostheses allowing endovascular placement have come into use as an effective, minimally invasive method of repairing damaged or diseased vessels, especially major blood vessels such as the aorta. These prostheses are comprised of one or more sleeves of fabric-like graft material, such as polyester (e.g., DACRON®, a trademark of DuPont Nemours and Co.), PTFE or collagen and metallic stents which are secured to the vessel wall to prevent-migration of the prosthesis, maintaining an open lumen therethrough, and to serve to seal the respective ends of the sleeve to the vessel wall to prevent leakage of blood around the sleeve ends to the outside of the sleeve. Proper sealing is especially critical when the prosthesis is used to bridge a segment of blood vessel that has been seriously compromised and can no longer prevent extravasation, such as in the case of an abdominal aortic aneurysm (AAA), a leading indication for prosthesis placement. The stents frequently include one or more barbs or projections that help anchor the prosthesis at the deployment site and prevent migration or trauma to the aortic neck.

The stents used to anchor the prosthesis, maintain an open lumen throughout, and seal the sleeve end, are preferably of the self-expanding stent type. The Z-Stent™ (Cook Incorporated, Bloomington, Ind.) and other closely related zig-zag stents of the same basic pattern are used in a number of AAA endovascular grafts due to their excellent expansion ratio and ability to compress into a relatively small introducer catheter, such as 18–20 Fr (6.0–6.7 mm) for deployment through a small cut down, or percutaneous puncture to, an access vessel. These zig-zag stents have struts connected by bends. The zig-zag stents are sutured or secured along the sleeve and/or at the ends of the sleeve. In some devices, a stent is secured to the proximal end of the sleeve and the proximal end of the terminal stent is placed renally such that the top edge of the sleeve lies just below the renal arteries. Therefore, the terminal stent can be securely anchored near the renal arteries and being open, does not compromise blood flow to the renal arteries.

For deployment, the prosthesis is compressed into a deployment system. In one embodiment of a deployment system, the terminal stent is compressed and loaded in a tubular component of the deployment system. In the fully compressed state, the struts of the zig-zag stent are generally parallel, however during loading into the tubular structure, the bends do not assume a regular or even arrangement inside the cap. As a result, the compressed bends can become disoriented and entangled such that when the stent is deployed, the bends cannot fully expand and properly seal the vessel. This problem is greatly compounded if the terminal stent has barbs on some struts such that the barbs can snag the other struts, leading to an unacceptably high rate of deployment failure. In fact, this irregular orientation of bends during compression would be inherent in virtually any zig-zag stent or serpentine stent made of bent wires due to the properties of the wire, manufacturing techniques, variable degrees of stress held in the individual bends, etc., that would not allow for a predictable compression to a desired target orientation by standard means. The recent addition of barbs to terminal stents of prostheses, such as for the AAA repair, has especially brought about an appreciation of this problem and the search for a solution.

SUMMARY OF THE INVENTION

The foregoing problems are solved and a technical advance is achieved in an illustrative stent having the terminal bends angled with respect to each other in a loaded or compressed configuration such that the respective bends, including barbs, do not become entangled with one another during expansion of the stent. A further clinical advantage of this configuration is that the stent can be further compressed than would be otherwise possible with a random configuration of bends such that the stent can be introduced via a smaller diameter delivery system.

In one aspect of the invention, the individual apices of the bends are plastically deformed into the angled arrangement by twisting the terminal portions of the bends from their original orientation, in which all struts in cross-section generally lie end-to-end in a circular configuration, to an orientation where the angled apices or fillets overlap by a consistent amount (i.e, a fan blade-like arrangement) to provide increased separation between struts of adjacent bends. Another advantage of this configuration is that the struts can be brought in closer proximity to the center, thereby allowing reduction of the size of the delivery system. Bending of the apices can occur in a jig wherein pins and clamps secure adjacent bends, while an opposite bend is laterally twisted with an articulating pin and clamp to produce the final orientation of bends.

In a second aspect of the invention, the terminal apices of the stent are interconnected by a suture, thread, or other tying means and drawn together for loading into the introducer system. When the suture is threaded through each fillet in an identical manner (e.g., outside to inside), it forces the respective fillets to twist in the same direction as they are drawn together. While keeping the ends drawn tight, the stent is loaded into a tubular component of the delivery system. Preferably, an eyelet or viewing portal in the side of the introducer is used to ascertain that all of the apices are visible and properly aligned. The suture is removed after the stent is loaded. This method of loading produces the same orientation of the terminal apices as in the pre-twisted configuration without having to plastically deform the bends. Other methods for either permanently or temporarily orienting the bends into an angled arrangement are contemplated to achieve a similar goal.

BRIEF DESCRIPTION OF THE DRAWINGS

Embodiments of the present invention will now be described by way of example with reference to the accompanying drawings, in which.

DETAILED DESCRIPTION

Figure 1:
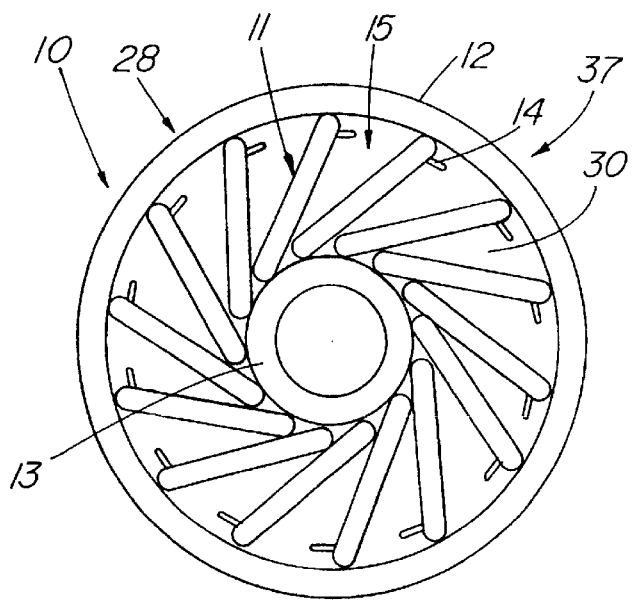
FIG. 1 depicts a partially-sectioned top view of the stent of the present invention while loaded in a delivery system.
Figure 2A:
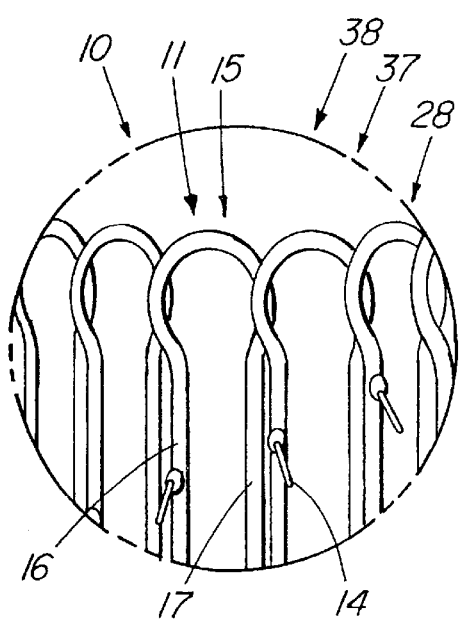
FIG. 2A depicts an enlarged view of a position of stent of FIG. 2
Figure 2:
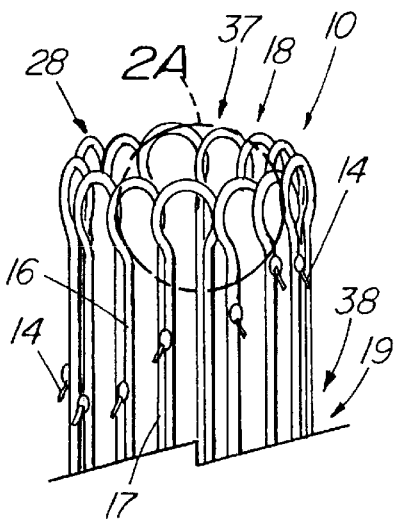
FIG. 2 depicts a side view and enlarged view of the stent of FIG. 1
Figure 6:
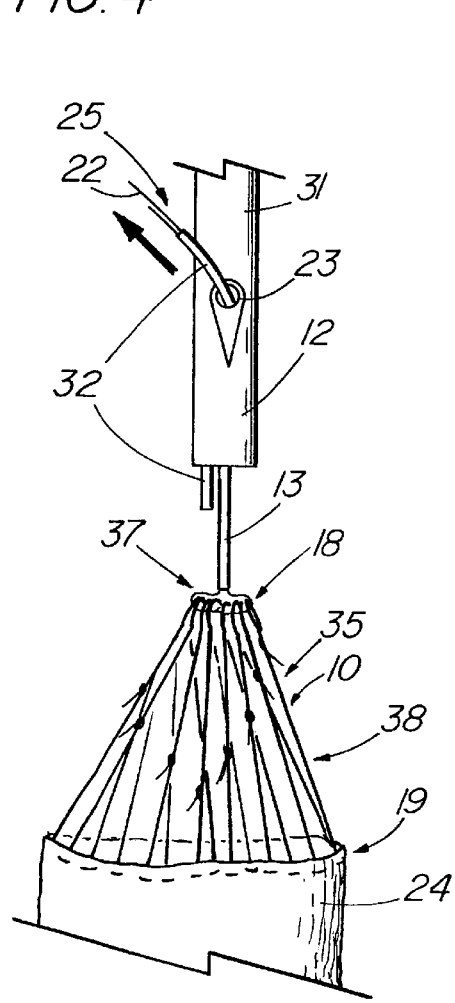
FIGS. 5–6 depict a side view of a stent being manipulated into the orientation of the present invention.

Referring now to FIGS. 1–2, the present invention comprises a stent 10, e.g., a modified Z-stent (Cook Incorporated, Bloomington, Ind.) or other zig-zag or serpentine-type stent 38 having a plurality of adjacent bends 15 comprising a first and a second strut 16,17 that unite at an apex 11, which in the illustrative embodiment is a hairpin turn for reducing bending stresses. Other embodiments of the apex 11 include a simple bend or a complete or 'safety pin' turn. The apices 11 generally align within a single plane at the first end 18 of the stent 10, while the apices 11 of the oppositely oriented bends 15 are similarly aligned at the second end 19 of the stent. The novelty lies in that the apices 11 of the terminal bends 15 of at least one end are generally deformed or twisted into a fan blade-like arrangement 28 inside a delivery system 12 which in the illustrative example of an expandable stent graft prosthesis 35 for repairing abdominal aortic aneurysms (AAA), comprises a top cap 31 of the introducer as depicted in FIG. 6. By 'deformed' it is meant that the apices have been manipulated prior to, during, or following compression of the expandable stent such that the twisted, fan blade-like arrangement is not the result of natural orientation of the apices during compression. Of course, the chances of a true fan blade-like arrangement of the apices occurring spontaneously during compression of the stent is infinitesimally small, particularly when the stent design includes six or more bends and apices.

Figure 3:
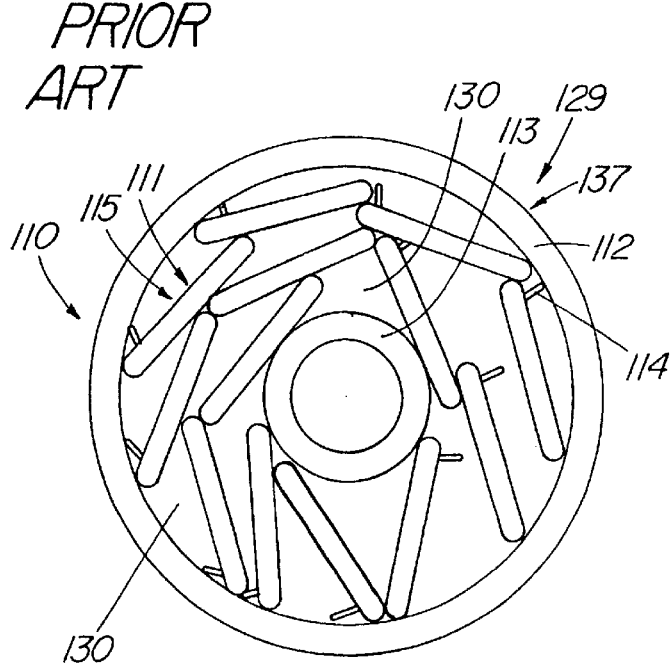
FIG. 3 depicts a partially-sectioned top view of a Prior Art stent loaded by a standard method.
Figure 4:
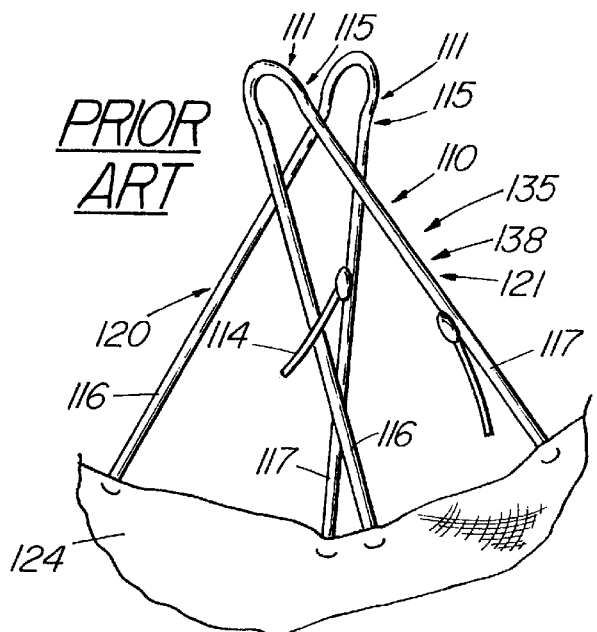
FIG. 4 depicts a side view of entangled bends of a Prior Art stent.
Figure 5A:
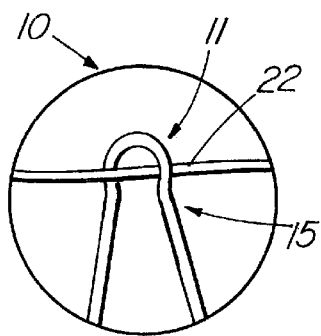
FIG. 5A depicts a enlarged view of a position of the stent of FIG. 5

The fan blade-like arrangement 28 of the apices 11 of the bends 15, depicted in FIG. 1, has several clinical advantages over a random orientation 129, an example of which is depicted in FIG. 3. The random orientation 129, which is the natural result of compressing a zig-zag type stent, results as the apices 111 come together during compression of the stent 110 and deflect at differing angles, leaving no consistent, regular pattern. The primary disadvantage of this random arrangement of bends 115 within the delivery system 112 is that the bends 115 can become entangled as the stent 110 is deployed. Deployment testing has revealed that in certain stent designs, entanglement can occur in a large percentage of the attempts and does not appear to be related to the experience of the operator. Probably the highest rate of entanglement is found in stents having barbs 14, 114, as shown FIGS. 1–4. FIG. 4 depicts a typical situation in which adjacent bends 115 of a zig-zag stent 110 attached to tubular graft prosthesis 124 are entangled due to the barb 114 of the second strut 117 of the first bend 120 ensnaring the first strut 116 of the second bend 121. The result is that the stent 110 cannot fully expand and thus, does not effectively seal the top of the graft 124 to prevent leakage of blood. Leakage can be due in part to the distortion from the entangled bends 115 and can cause the first stent of the graft (directly beneath the suprarenal stent) to pull away from the vessel wall. Barbs 114 can also ensnare the opposite leg of the same bend, creating a crossed-over, figure eight-like configuration. Additionally, the apex 111 of one bend 115 can entangle with the apex of an adjacent bend 115, without the barb 114 being involved. As depicted in FIG. 1, angling the apices 11 causes increased distance between adjacent struts and therefore, separates the barbs 14 from the struts. The distance is maintained during stent expansion such that entanglements are greatly reduced or eliminated. Besides the problem of leakage, there is a risk that entangled bends, which in a suprarenal stent for AAA repair, can cause sufficient obstruction of a renal artery to cause damage to the kidney. This may also be a problem in stents for peripheral vessels in which a side branch may be obstructed if proper expansion does not occur.

Another advantage of the fan blade-like arrangement is the ability to further compress the stent as compared with a loaded stent having randomly oriented bends as depicted in FIG. 3. The apices 11 of a loaded stent of FIG. 1 provide a much more efficient filling of the annular space 30 lying between the inside surface of the delivery system 12 and the outside surface of the inner cannula 13. For example, in the random orientation 129 depicted in FIG. 3, the stent is jammed into the delivery system 112 with little, if any, additional room spare due to irregular bunching of the bends 115. If the delivery system 112 of FIG. 3 is used with a stent 10 having the fan blade-like arrangement 28 of FIG. 1, the bends 15 would not fully extend to the inner cannula 13, making further reduction in the diameter of the delivery system 12 possible. A smaller diameter introducer offers several potential clinical benefits. Naturally, a smaller introducer requires a smaller puncture of the vessel. For example, if the introducer can be sufficiently small for placement of endovascular stent grafts, the usual femoral artery cutdown procedure can be replaced by percutaneous entry, involving much less trauma to the patient. Other potential advantages to downsizing the delivery system include less disruption of atheroma and plaque which could lead to emboli, less disruption of blood flow, and less likelihood of damage to the vessel wall.

There are multiple methods of obtaining the fan blade-like arrangement 28 of the bends shown in FIG. 1. One method is to manipulate the stent 10 in a jig or similar restraining device. For example, the apices 11 of adjacent bends 15 can be placed over pins on a flat fixture and clamped stationary, while the oppositely facing bend therebetween can be independently clamped and rotated to plastically deform the metal to the desired amount of twist. The position along the length of the stent where it is clamped determines whether the twist is limited to the area of the apices, or occurs more gradually over a longer distance. Determining the amount of twist used in the jig to achieve the desired angle must take into account the resiliency of the metal. Once it is established by experimental means for a particular stent design and bending fixture, it can be controlled and repeated for each bend. When the plastically deformed stent is compressed for loading, the angled bends 15 and apices 11 then assume the desired configuration of FIG. 1. A side hole 23, as shown in FIG. 6, allows visual confirmation that the desired orientation has been achieved.

Figure 5:
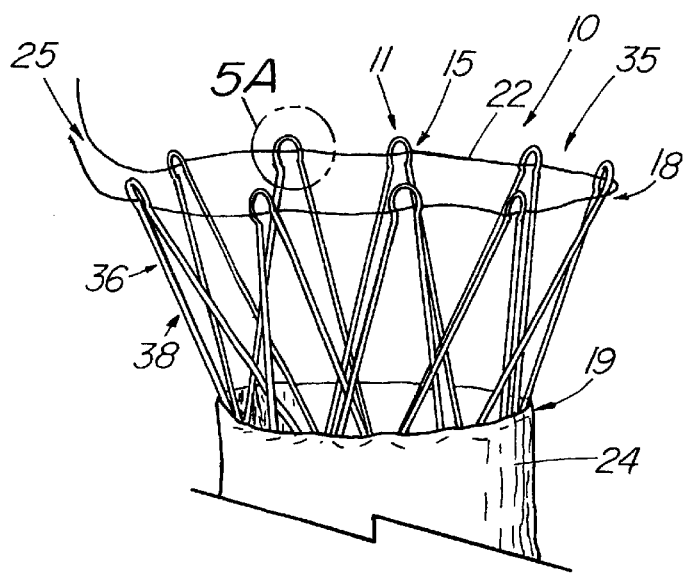

A second method of obtaining the fan blade-like arrangement is illustrated in FIGS. 5–6. As depicted in FIG. 5, an elongate constraining means 22, such as a piece of suture material, is looped through the apices 11 of the suprarenal stent 10 in the manner shown in the detail of FIG. 5. Of course any similar implement such as a suitable thread, string, strand, thin wire, fishing line, etc. can be used as a elongate constraining device 22. By sequentially feeding the end 25 of the suture 22 from the outside to the inside of each apex 11, the suture 22 applies the same direction force on each bend of the stent 10 as the ends 18 of the stent 10 are drawn together as depicted in FIG. 6, thus forcing the apices to twist into the orientation depicted in FIG. 1. To draw the ends 18 of the bends 15 together, the ends 25 of the suture 22 are fed through the tubular constraining device 31, such as the top cap of the delivery system 12, restraining the stent 10 and then out through the side passage 23 or eyelet in the side of the delivery system. To facilitate this procedure, a conduit 32, such as a piece of flexible tubing, can be fed through the eyelet 23 to the proximal end of the top cap 31. The suture material 22 is then fed into the conduit 32 and out the eyelet 23. The conduit 32 is then discarded. The ends 25 of the suture 22 are then pulled tight, or one of the ends 25 is pulled while the other is maintained in place, while the ends 18 of the stent 10, now being drawn into the fan blade-like arrangement 28, are inserted into the proximal end of the top cap 31 of the delivery system 12. The suture 22 is removed through the eyelet 23 which also serves as a viewing portal for confirming the proper orientation of the apices 11 as loaded. The remainder of the graft prosthesis 24 is compressed and loaded into another part of the delivery system (not shown). In a graft prosthesis 24 as depicted, only the first or distal end 18 is oriented into the fan blade-like arrangement 28, since the second end 19 is sewn or otherwise attached to the graft prosthesis 24 material, obviating the problem of the bends 15 becoming entangled during expansion. If a zig-zag or other type of stent lacks the graft prosthesis 24, entanglements can occur at both ends; therefore, there is probable benefit in orienting the second end 19 into the fan blade-like arrangement 28 as well.

The degree of twist of the apices can be uniform along the length of the stent or can vary longitudinally. In an example of the latter, the angle 27 of the twist might be 80° at the first end 18 of the stent, but gradually diminishes toward the second end 19 of the stent as the second strut 17 of a bend 15, which had been forced out of circumferential alignment with the first strut 16, is allowed to reassume the original, untwisted configuration, thereby being more aligned to the other struts 16,17 along the outer circumference 26 of the stent. Alternatively, a clockwise twist at the first end 18 can be reversed such that the second end 19 includes a counter-clockwise twist.

Figure 7:
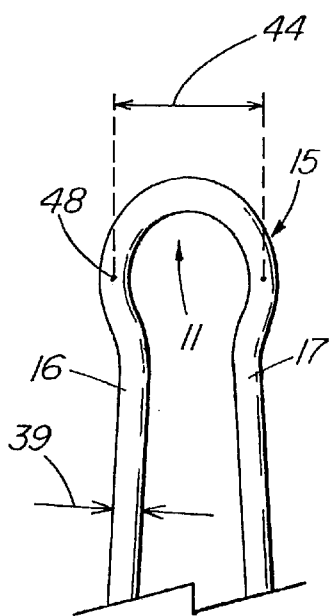
FIG. 7 depicts a enlarged side view of a bend of the stent of the present invention.
Figure 8:
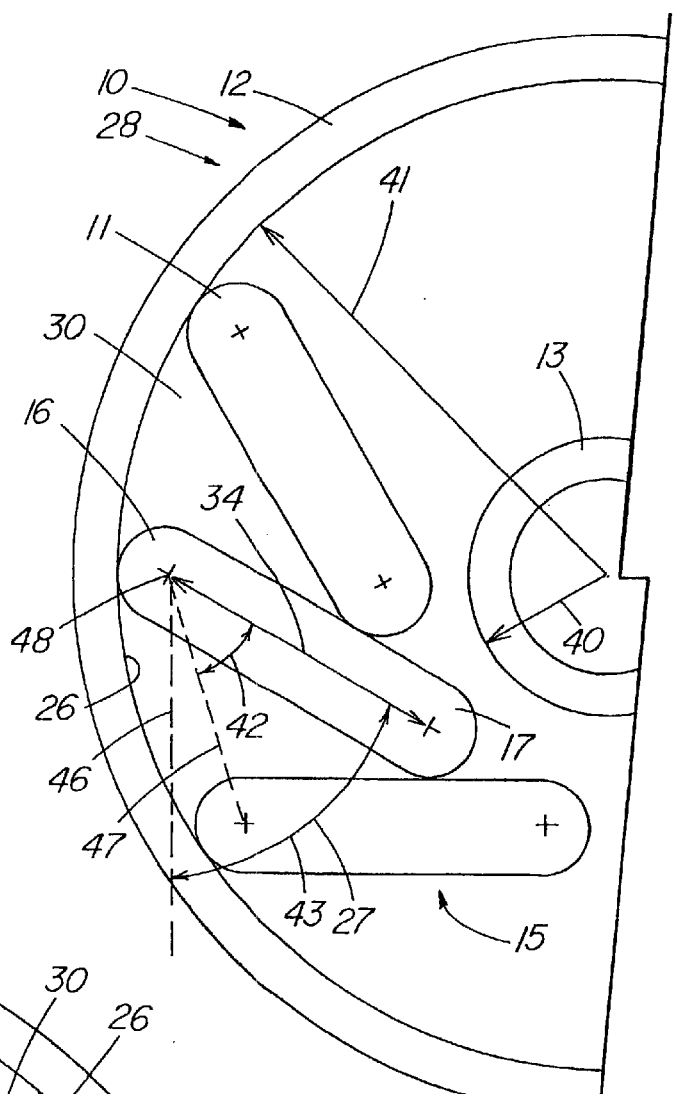
FIGS. 8–9 depict partially-sectioned top view of the stent of the present invention while loaded in a delivery system.
Figure 9:
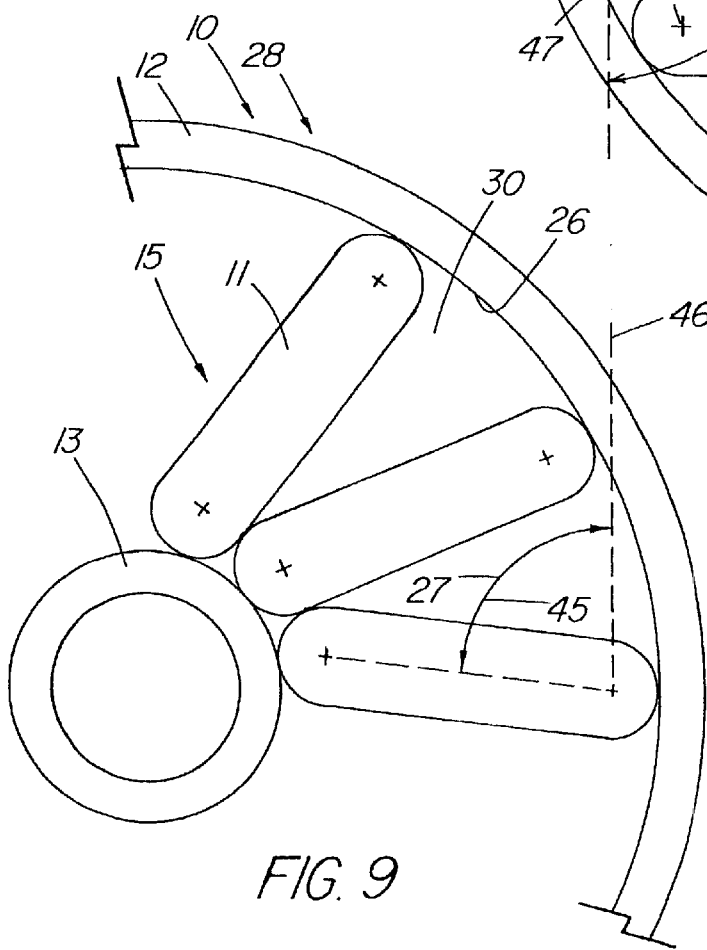

Mathematical calculations can be used to determine the practical range of angles that the apices 11 of the bends 15 can assume to produce reliable, entanglement-free deployment, given the particular parameters of the stent. To calculate the range that the angle 27 can assume, a number of parameters must be known, including the number of points or apices 11, the width of the wire comprising the bends 15, the width of the apex 11, the inside radius of the constraining device (delivery system) 12, and the outside radius of the inner cannula 13. While the angles useful to produce entanglement-free expansion can range from 10° to 90°, it is usually preferred to have an angle 27 at the higher end of that range, i.e., 50°–85°, to minimize entanglement. By way of example and using FIGS. 7–9 as reference, the following equations are provided for calculating the minimum angle 43 and maximum angle 45 (twist angle 27) for a stent having the following parameters:

$$\alpha_2 = \frac{180\left(\alpha_1 + \mathrm{Sin}\left[\frac{\pi}{n}\right]\right)}{\pi}$$

$r_1$=outside radius (40) of inner cannula (13)=0.635 mm
$r_2$=inside radius (41) of constraining device (12)=2.5 mm
$r_3$=one half the diameter ($2r_3$) of the stent wire=0.23 mm
n=number of apices (11)=12
d=width of apex (center to center of wire)=1.43 mm With these known parameters an equation can be used to solve for angle 42 which is designated $\alpha_1$, this angle being measured between line 47 (which intersects the centers 48 of adjacent struts 16) and the centerline 34 of the apex 11 of the bend 15. This equation is as follows:

$$O = 2r_3\mathrm{Cos}\left[\frac{2\pi}{n}\right] - 2(r_2 - r_3)\mathrm{Sin}\,\alpha_1\,\mathrm{Sin}\left[\frac{\pi}{n}\right] - \left(-d + 2(r_2 - r_3)\mathrm{Cos}\,\alpha_1\,\mathrm{Sin}\left[\frac{\pi}{n}\right] - 2r_3\mathrm{Sin}\left[\frac{2\pi}{n}\right]\right)\mathrm{Tan}\left[\frac{2\pi}{n}\right]$$

Solving for $\alpha_1$ using the above parameters, a value of 1.03911 (radians) is obtained, which is the smaller of the two values obtained using the sine function of the equation. This value can be used to solve a second equation for determining the minimum possible angle 43, or $\alpha_2$, (expressed in degrees) for a particular stent, the equation being:

The maximum possible angle 45, or $\alpha_3$ (also expressed in degrees), can be obtained using a third equation:

$$\alpha_3 = \frac{180\left(\frac{\pi}{2} - \mathrm{ArcCos}\left[\frac{d^2 + (r_2 - r_3)^2 - (r_1 + r_3)^2}{2d(r_2 - r_3)}\right]\right)}{\pi}$$

Using 1.03911 as the value for $\alpha_1$, minimum angle $\alpha_2$ is found to be 74.4° and the maximum angle $\alpha_3$ is 83.4°. It should be noted that in some instances, there can be no maximum angle if the width 44 of the apex (value d) is too small relative the annular space 30 located between the constraining device 12 and the inner cannula 13, or if there is no inner cannula 13. For example, if in the above example, the value for d is reduced to 1.34, producing a value for $\alpha_1$ of 0.769, the equation for the maximum angle 45 cannot be solved because the apex 11 will not touch the inner cannula 13, even at a full 90° angle.

Variation of this angle within a single fan blade-like arrangement is permitted. For example, the angles of the individual apices at one end of the stent could vary as much as 15–20° and would be considered substantially the same, thus falling within the scope of this invention, although it is prefered to limit this variation to 10° or less. The important factor is that the apices are configured in a fan blade-like arrangement with each being oriented in the same direction to reduce the possibility of entanglement. It should be noted that in the example of FIG. 8, the twist of the fan blade-like arrangement 28 is considered to be counter-clockwise, however, a clockwise twist could be used (not shown), the difference being that line 47 would intersect adjacent second struts 17, now located toward the outer circumference 26 of the stent, rather than intersecting adjacent first struts 16 being so oriented. The angle 42 for $\alpha_1$ would still be calculated from lines 34 and 47, both now originating from the centers 48 of the second strut 17.

Finally, it should be noted that the above equations and methods for calculating the range of angles are exemplary and not required to practice the invention. Alternative methods of determining the desired angle may be used. It should also noted that the illustrative stents and described methods for obtaining the fan blade-like arrangement are for purpose of example only and other stent types and methods or orienting the bends can be used without departing from the spirit of this invention.

What is claimed is:

1. A stent capable of assuming both an expanded configuration and a compressed configuration, the stent comprising:

a first end and a second end;

a plurality of bends comprising an apex interconnecting a first and a second strut, the apices of the plurality of bends located about at least one of the first end and the second end of the expandable stent;

wherein the apices about the at least one of the first end and the second end are deformed into a fan blade-like arrangement when the stent is in the compressed condition and being viewed from the at least one of the first end and the second end, whereby each of the apices of the at least one of the first end and the second end are oriented at an angle with respect to the outer circumference of the stent, the angle being substantially the same for each of the apices of the at least one of the first end and the second end; and wherein the apices of the fan blade-like arrangement are such that the first strut of each of the plurality of bends overlaps the second strut of the adjacent one of the plurality of bends.

2. The stent of claim 1 wherein the apices comprising the fan blade-like arrangement are plastically deformed such that the angle of the apices is present in both the expanded and the compressed conditions of the stent.

3. The stent of claim 1 wherein the apices comprising the fan blade-like arrangement are elastically deformed such that the angle of the apices is present only in the compressed condition of the stent.

4. The stent of claim 1 wherein the stent comprises a zig-zag configuration.

5. The stent of claim 1 further comprising a plurality of struts that are interconnected by at least one of the plurality of bends.

6. The stent of claim 5 wherein the stent includes at least one barb located on one or more of the struts.

7. The stent of claim 1 wherein the stent further includes a tubular graft prosthesis attached thereto.

8. The stent of claim 7 wherein the second end of the stent is attached to the tubular graft prosthesis, while the first end remains at least partially uncovered by the tubular graft prosthesis with the fan blade-like arrangement comprising the first end of the stent.

9. The stent of claim 1 further including a delivery system that constrains the stent into the compressed condition.

10. The stent of claim 9 wherein the delivery system further includes a tubular component to constrain the first end of the stent.

11. The stent of claim 1 wherein the fan blade-like arrangement comprises both the first and the second ends of the stent.

12. The stent of claim 1 wherein the variation between the angles of the apices at the at least one of the first end and the second end is no more than 20°.

13. The stent of claim 1 wherein the angle of orientation of the apices is at least 50°.

14. An expandable graft prosthesis capable of assuming both an expanded configuration and a compressed configuration, the graft prosthesis comprising:

at least one expandable stent that includes a first end and a second end, the stent further including a plurality of bends comprising an apex interconnecting a first and a second strut, the apices of the plurality of bends located about at least one of the first end and the second end of the expandable stent;

a tubular graft prosthesis attached to the at least one expandable stent such that the apices about the at least the first end and the second end of the expandable stent extend beyond an edge of the tubular graft prosthesis;

wherein each of the apices about the at least one of the first end and the second end are configured in a fan blade-like arrangement when the stent is in the compressed condition and being viewed from the at least one of the first and the second end, whereby each of the apices of the at least one of the first end and the second end being are oriented at an angle with respect to the circumference of the stent, the angle being substantially the same for each of the apices at the at least one of the first end and the second end; and wherein the apices of the fan blade-like arrangement are such that the first strut of each of the plurality of bends overlaps the second strut of the adjacent one of the plurality of bends.

15. The prosthesis of claim 14 wherein only the first end of the expandable stent comprises the fan blade-like arrangement.

16. The prosthesis of claim 14 wherein the device further includes a delivery system for constraining the expandable stent into the compressed condition.

17. The prosthesis of claim 16 wherein the delivery system further includes a tubular component to constrain the first end of the stent.

18. The stent of claim 14 wherein the variation between the angles of the apices at the at least one of the first end and the second end is no more than 20°.

19. The prosthesis of claim 14 wherein the angle of orientation of the plurality of apices is at least 50°.

20. The prosthesis of claim 14 wherein the angle of orientation comprising the fan blade-like arrangement is a result of plastic deformation of the apices such that the angle of the apices is present in both the expanded and the compressed conditions of the stent.

21. An expandable graft prosthesis capable of assuming both an expanded configuration and a compressed configuration, the graft prosthesis comprising:

at least one expandable stent that includes first end and a second end, the stent further including a zig-zag stent having plurality of bends comprising an apex interconnecting a first and a second strut, the bends terminating about either the first end and the second end of the expandable stent to form a plurality of apices;

one or more outwardly projecting barbs attached to at least one of the first and second strut of at least selected ones of the plurality of bends;

a tubular graft prosthesis attached to the expandable stent such that the apices at the first end of the expandable stent extend beyond the edge of the tubular graft prosthesis;

a delivery system that constrains the expandable stent into the compressed condition;

wherein each of the apices about the first end are configured in a fan blade-like arrangement when the stent is in the compressed condition and being viewed from the first end, whereby each of the apices of the first end are oriented at an angle with respect to the circumference of the stent, the angle being substantially the same for each of the apices at the first end; and wherein the apices of the fan blade-like arrangement are such that the first strut of each of the plurality of bends overlaps the second strut of the adjacent one of the plurality of bends.

22. A method for orienting an expandable stent that includes a plurality of apices and a first end into a fan blade-like arrangement of the plurality of apices, each having a first and a second side, and loading the stent inside a tubular constraining device having a proximal end and a passageway, comprising the steps of:

1. feeding a selected end of an elongate constraining means having a first end and a second end through the apex of a first bend of a stent, the direction of feeding coming from one of the outside or the inside of the apex;
2. feeding the selected end through the apex of a second, adjacent bend, the direction of feeding being that which is selected in step 1;
3. repeating the sequence of sequentially feeding the selected end through the next one of the plurality of apices from the direction of feeding selected in step 1 until the elongate constraining means has been fed through each of the plurality of apices;
4. applying force against at least one of the first end and the second end of the elongate constraining means, thereby drawing the plurality of apices at the first end together into a fan blade-like arrangement; and
5. constraining the first end of the stent within a tubular constraining device.

23. The method of claim 22 further including a sixth step of removing the elongate constraining means from the plurality of apices.

24. The method of claim 23, further including the steps between steps 3 and 4 comprising:

3a. Feeding the selected end of the elongate constraining means through the proximal end and into the passageway; and
3b. Feeding the selected end out of the passageway via a side passage through the wall of the tubular constraining device.

25. The method of claim 24 wherein step 4 further includes applying force to both the first and second ends of the elongate constraining means to draw the apices together into the fan blade-like arrangement.

* * * * *